US012716088B2

(12) United States Patent
Niinivaara et al.

(10) Patent No.: US 12,716,088 B2
(45) Date of Patent: Aug. 25, 2026

(54) METHOD AND SYSTEM FOR PERFORMING A CUMULATIVE NUCLEIC ACID AMPLIFICATION REACTION

(71) Applicant: Gen-Probe Incorporated, San Diego, CA (US)

(72) Inventors: Anne Niinivaara, Vantaa (FI); Juha Saharinen, Espoo (FI); Juha Kirveskari, Espoo (FI)

(73) Assignee: GEN-PROBE INCORPORATED, San Diego, CA (US)

( * ) Notice: Subject to any disclaimer, the term of this patent is extended or adjusted under 35 U.S.C. 154(b) by 403 days.

(21) Appl. No.: 18/037,543

(22) PCT Filed: Nov. 24, 2021

(86) PCT No.: PCT/FI2021/050805
§ 371 (c)(1),
(2) Date: May 17, 2023

(87) PCT Pub. No.: WO2022/112655
PCT Pub. Date: Jun. 2, 2022

(65) Prior Publication Data

US 2024/0301479 A1 Sep. 12, 2024

(30) Foreign Application Priority Data

Nov. 24, 2020 (FI) ..................................... 20206199

(51) Int. Cl.
*C12Q 1/6851* (2018.01)
*C12Q 1/6848* (2018.01)

(52) U.S. Cl.
CPC ................................. *C12Q 1/6851* (2013.01)

(58) Field of Classification Search
None
See application file for complete search history.

(56) References Cited

U.S. PATENT DOCUMENTS

| | | | | |
|---|---|---|---|---|
| 6,605,451 | B1 | 8/2003 | Marmaro et al. | |
| 8,133,703 | B2 | 3/2012 | Ching et al. | |
| 8,512,955 | B2 | 8/2013 | Brentano et al. | |
| 8,628,923 | B2 | 1/2014 | Hamilton et al. | |
| 10,648,025 | B2 | 5/2020 | Allawi et al. | |
| 2009/0069194 | A1* | 3/2009 | Ramakrishnan | C12Q 1/6851 435/6.12 |
| 2009/0082225 | A1* | 3/2009 | Gerdes | C12Q 1/6806 536/25.4 |
| 2013/0184169 | A1 | 7/2013 | Klass et al. | |
| 2014/0206578 | A1* | 7/2014 | Gumbrecht | C12Q 1/6851 204/403.01 |
| 2017/0327867 | A1 | 11/2017 | Dohale et al. | |

FOREIGN PATENT DOCUMENTS

| | | | |
|---|---|---|---|
| EP | 1658898 | | 5/2006 |
| EP | 1658898 | A1 | 5/2006 |
| EP | 2016186 | B1 | 1/2013 |
| WO | 9727324 | | 7/1997 |
| WO | 9727324 | A1 | 7/1997 |
| WO | 2006136990 | | 12/2006 |
| WO | 2006136990 | A2 | 12/2006 |
| WO | 2007130951 | A2 | 11/2007 |
| WO | 2010149861 | | 12/2010 |
| WO | 2010149861 | A1 | 12/2010 |
| WO | 2013171140 | A1 | 11/2013 |
| WO | 2016044673 | | 3/2016 |
| WO | 2016044673 | A1 | 3/2016 |
| WO | 2020104390 | A2 | 5/2020 |

OTHER PUBLICATIONS

Finnish Patent Office Search Report dated May 20, 2021 in the corresponding Finnish Application No. 20206199 (2 pages).
Finnish Patent Office Action dated May 20, 2021 in the corresponding Finnish Application No. 20206199 (10 pages).
Finnish Patent Office Action dated Jan. 19, 2023 in the corresponding Finnish Application No. 20206199 (7 pages).
Andersson et al., “Properties of targeted preamplification in DNA and cDNA quantification.” Expert Review of Molecular Diagnostics, 2015, 15:8, 1085-1100. (17 pages).
Houssin et al., “Ultrafast, sensitive and large-volume on-chip real-time PCR for the molecular diagnosis of bacterial and viral infections.” Lab Chip 2016, vol. 16, 1401-1411. (11 pages).
Keller et al., “Automated Forensic Animal Family Identification by Nested PCR and Melt Curve Analysis on an Off-the-Shelf Thermocycler Augmented with a Centrifugal Microfluidic Disk Segment.” PLOS One 2015, 10(7), e0131845. (18 pages).
Quan et al., “dPCR: A Technology Review.” Sensors, 2018, vol. 18, 1271. (27 pages).
Houssin, T., et al., “Ultrafast, sensitive and large-volume on-chip real-time PCR for the molecular diagnosis of bacterial and viral infections,” Lab Chip 16:1401-1411, 2016.
Keller, M., et al., “Automated Forensic Animal Family Identification by Nested PCR and Melt Curve Analysis on an Off-the-Shelf Thermocycler Augmented with a Centrifugal Microfluidic Disk Segment,” PLoS One 10(7):e0131845, 2015, 18 pages.

(Continued)

*Primary Examiner* — Robert T. Crow
(74) *Attorney, Agent, or Firm* — Sherbina Intellectual Property; Nicholas V. Sherbina; Jeffrey E. Landes

(57) ABSTRACT

The present disclosure is directed to a nucleic acid amplification based method for determining the presence or absence of a target polynucleotide in a sample, wherein a portion of the amplified reaction mix is replaced with a further portion of the sample between pre-amplification steps to obtain a mix of an amplified reaction and an unamplified sample. The present disclosure thus provides a cumulative amplification reaction for highly sensitive detection of target polynucleotides. The present disclosure is also directed to a nucleic acid amplification reaction system for performing such a cumulative amplification reaction.

10 Claims, 2 Drawing Sheets

(56) References Cited

OTHER PUBLICATIONS

Quan, P.-L., et al., "dPCR: A Technology Review," Sensors 18:1271, 2018, 27 pages.

Examination Report dated Dec. 22, 2025, issued in corresponding European Application No. 21819163.3, filed Nov. 24, 2021 (12 pages).

Basu, A.S., "Digital Assays Part I: Partitioning Statistics and Digital PCR," SLAS Technol. 22:369-386, 2017.

Examiner's Requisition dated Jan. 8, 2026, issued in corresponding Canadian Application No. 3,202, 119, filed Nov. 24, 2021 (9 pages).

Examination Report dated Nov. 12, 2025, issued in corresponding Australian Application No. 2021388987, filed Nov. 24, 2021 (5 pages).

* cited by examiner

| Sample name | COU ID | CALL | CONTAIN: VIM | CONTAIN: KPC | HYB-2 CTRL_NVD_HYB_001 | HYB-2 Grid | HYB-2 Pm_GES_01 (CRB) | HYB-2 Pm_GES_02 (CRB) | HYB-2 Pm_GES_03 (CRB) | HYB-2 Pm_GES_04 (ESBL) | HYB-2 Pm_GES_05 (ESBL) | HYB-2 Pm_GES_06 | HYB-2 Pm_GES_06b | HYB-2 Pm_OXA-24_02a | HYB-2 Pm_OXA-24_02b | HYB-2 Pm_OXA-27_03a | HYB-2 Pm_OXA-27_03b | HYB-2 Pm_OXA-48_04 | HYB-2 Pm_OXA-51_01 | HYB-2 Pm_OXA-58_03a | HYB-2 Pm_OXA-58_03b | HYB-2 Pm_VIM_5 | HYB-2 Pm_VIM_6 | HYB-2 Pm_kpc_01 | HYB-2 Pm_kpc_02 | HYB-2 Pm_kpc_03 | HYB-2 Pm_oxa-48_01 | HYB-2 Pm_oxa-48_02 | HYB-2 Pm_vim_01 | HYB-2 Pm_vim_02 | HYB-2 Pm_vim_04 | HYB-2 Pma_orymod_01 | HYB-2 Pma_orymod_05 | HYB-2 empty |
|---|---|---|---|---|---|---|---|---|---|---|---|---|---|---|---|---|---|---|---|---|---|---|---|---|---|---|---|---|---|---|---|---|---|---|
| #1_11x6_20 cfu/ml VIM+KPC #D6 | 135951001 | UNKW | + | + | 5 | 18 | 0 | 1 | 1 | 0 | 0 | 0 | 0 | 0 | 0 | 0 | 0 | 1 | 0 | 0 | 0 | 7 | 1 | 5 | 5 | 7 | 0 | 0 | 6 | 7 | 0 | 1 | 0 | 8 |
| #2_11x6_20 cfu/ml VIM+KPC #D7 | 238557848 | UNKW | + | + | 7 | 18 | 0 | 0 | 0 | 0 | 0 | 1 | 0 | 0 | 0 | 0 | 0 | 0 | 1 | 1 | 0 | 7 | 1 | 7 | 7 | 6 | 0 | 0 | 7 | 7 | 0 | 0 | 1 | 7 |
| #3_11x6_20 cfu/ml VIM+KPC #D8 | 136145006 | UNKW | + | + | 6 | 18 | 0 | 0 | 0 | 0 | 0 | 0 | 0 | 0 | 1 | 1 | 0 | 0 | 1 | 0 | 0 | 0 | 0 | 7 | 7 | 7 | 0 | 0 | 2 | 0 | 0 | 1 | 1 | 8 |
| #4_11x6_20 cfu/ml VIM+KPC #D9 | 136260004 | UNKW | + | + | 7 | 17 | 0 | 1 | 1 | 0 | 0 | 1 | 0 | 0 | 0 | 0 | 0 | 0 | 0 | 1 | 0 | 7 | 1 | 7 | 7 | 7 | 0 | 1 | 6 | 7 | 1 | 0 | 0 | 10 |

Figure 2.

METHOD AND SYSTEM FOR PERFORMING A CUMULATIVE NUCLEIC ACID AMPLIFICATION REACTION

CROSS-REFERENCE TO RELATED APPLICATIONS

This application is a U.S. national phase entry of International Application No. PCT/FI2021/050805, filed Nov. 24, 2021, which claims priority to Finnish Application No. 20206199, filed Nov. 24, 2020.

FIELD

The present disclosure relates generally to methods for analyzing a sample for the presence of an analyte and more particularly, to methods for conducting nucleic acid amplification reactions, especially polymerase chain reactions (PCRs) as well as isothermal amplification reactions.

BACKGROUND

In nucleic acid amplification technologies including, but not limited to, polymerase chain reaction, PCR, a key question for detection sensitivity relates to the amount of template nucleic acid molecules introduced to the amplification reaction.

In order to increase sensitivity, the number of template molecules can be processed from a larger template sample volume by methods like concentration, for example by using size exclusion filter or other relevant methods, like nucleic acid precipitation. However, use of such methods both requires extra processing steps and often instruments, such as a centrifuge, as well can itself also concentrate molecular entities capable of inhibiting the nucleic acid amplification reaction.

Furthermore, in some cases, the input sample material is of amplification inhibiting in such amount that that it requires a further dilution step to overcome the inhibition, which concomitantly decreases the overall amplification reaction sensitivity.

Examples of sample matrices typically needed to be concentrated, include water system samples, human/animal tissues/excretions, like urine, cerebrospinal fluid, blood, sputum and bronchoalveolar lavage. Examples of sample matrices typically needed to be diluted due to amplification reaction inhibitory substances include stool, sputum, nasopharyngeal aspirates and blood or blood containing tissue samples. Examples of applications in the aforementioned areas include the methods for detection of the presence of microbes such as pathogens or antibiotic resistance thereof, circulating tumor cells (CTC), cfDNA, exosome/EV RNA, or somatic genotypes.

SUMMARY

The present disclosure provides methods and system for carrying out a cumulative amplification reaction in a reaction chamber by successive cycles of amplifying a reaction mixture comprising an aliquot of a sample and amplification reagents, and replacing a portion of the amplified reaction mixture with a further portion of the sample and the amplification reagents. In particular, the present embodiments allow amplification of increased sample volumes compared to the prior art methods, thus providing highly sensitive amplification method by carrying out successive amplifications of portions of the sample in a cumulative reaction.

Accordingly, in one aspect, the present disclosure provides a nucleic acid amplification method for determining the presence or absence of a target polynucleotide in a sample, the method comprising the steps of:

i) subjecting an amplification reaction mixture in a reaction chamber to conditions amplifying a target polynucleotide, wherein said reaction mixture comprises reagents necessary for nucleic acid amplification and an aliquot of the sample;
ii) replacing a portion of an amplified reaction mixture in said reaction chamber obtained from the amplification reaction of the previous step with a further unamplified aliquot of said sample and with further reagents necessary for nucleic acid amplification to obtain a mix of amplified reaction mixture and the unamplified sample;
iii) subjecting the reaction mixture in said reaction chamber obtained from step ii) to conditions amplifying a target polynucleotide; and
iv) optionally repeating a cycle of steps ii) and iii) a number of times required for subjecting a desired amount of the sample to the amplification reaction;
v) optionally detecting the presence or absence of an amplicon formed in the preceding amplification steps to determine the presence or absence of the target polynucleotide in the sample.

In a second aspect, the present disclosure provides a system for performing a cumulative amplification reaction, the system comprising:

a reaction chamber in fluidic communication with a sample reservoir and a waste reservoir, wherein said sample reservoir is arranged to receive a sample; and means for performing the steps of: (a) transferring a portion of the contents of the sample reservoir to the reaction chamber; (b) subjecting the contents of the reaction chamber to conditions supporting nucleic acid amplification reactions; (c) replacing part of the contents present in the reaction chamber with a further portion of the contents of said sample reservoir to obtain a mix of amplified reaction and the unamplified sample, wherein a volume of liquid, preferably corresponding to the volume of said further portion, is moved from the reaction chamber to the waste reservoir, and (d) repeating a cycle of steps (b) and (c) a number of times required for subjecting a desired amount of sample to the amplification reaction, wherein step (c) is performed at controlled intervals or continuously.

In a third aspect, the present disclosure provides a system for performing a cumulative amplification reaction, the system comprising:

a reaction chamber in fluid communication with a sample reservoir, a waste reservoir, and a reagent reservoir containing a master mix comprising nucleic acid amplification reagents, wherein said sample reservoir is arranged to receive a sample and is in fluidic communication with the reaction chamber; and means for performing the steps of: (a) transferring a portion of the sample from the sample reservoir and a portion of the master mix from the reactant reservoir to the reaction chamber; (b) subjecting the contents in the reaction chamber to conditions supporting nucleic acid amplification reactions; (c) replacing part of the contents of the reaction chamber with further portions of the sample and master mix to obtain a mix of amplified reaction and the unamplified sample, wherein a volume of liquid, preferably corresponding to the volumes of said further portions of the sample and master mix, is moved from the reaction chamber to the waste reservoir, and (d) repeating a cycle of steps (b) and (c) a number of times required for subjecting a desired amount of the sample to the amplification reaction, wherein step (c) is performed at controlled intervals or continuously.

In a fourth aspect, the present disclosure provides a nucleic acid amplification method for determining the presence or absence of a target polynucleotide in a sample, the method comprising the steps of:

i) subjecting an amplification reaction mixture in a reaction chamber to conditions amplifying a target polynucleotide, wherein said reaction mixture comprises reagents necessary for nucleic acid amplification and an aliquot of the sample;
ii) replacing the amplified reaction mixture in said reaction chamber obtained from the amplification reaction of the previous step with a further unamplified aliquot of said sample and with further reagents necessary for nucleic acid amplification, wherein said amplified reaction mixture is moved to a store reservoir;
iii) subjecting the reaction mixture comprising said unamplified aliquot in said reaction chamber to conditions amplifying a target polynucleotide;
iv) repeating a cycle of steps ii) and iii) a number of times required for subjecting a desired amount of the sample to the amplification reaction;
v) subjecting an aliquot of the amplified reaction mixture present in said store reservoir to a further amplification reaction in order to detect a product pre-amplified in steps ii) and iii).

In a fifth aspect, the present disclosure provides a system for performing a cumulative amplification reaction, the system comprising:

a reaction chamber in fluidic communication with a sample reservoir and a store reservoir, wherein said sample reservoir is arranged to receive a sample; and means for performing the steps of: (a) transferring a portion of the contents of the sample reservoir to the reaction chamber; (b) subjecting the contents of the reaction chamber to conditions supporting nucleic acid amplification reactions; (c) replacing the contents present in the reaction chamber with a further portion of the contents of said sample reservoir transferred to the reaction chamber, wherein a volume of liquid present in the reaction chamber is moved from the reaction chamber to the store reservoir, (d) repeating a cycle of steps (b) and (c) a number of times required for subjecting a desired amount of the sample to the amplification reaction, wherein step c) is performed at desired intervals or continuously, and (e) subjecting an aliquot of the amplified reaction mixture present in said store reservoir to a further amplification reaction.

In the sixth aspect, the present disclosure provides a computer program comprising instructions or software code adapted to perform or control the performance of the methods or the system as defined above or a computer program comprising instructions which, when the program is executed by a computer, cause the computer to control the performance of the steps of the methods as defined above.

BRIEF DESCRIPTION OF THE DRAWINGS

FIG. 2. Example of a hybridization detection after cPCR protocol. In the experiment, sample concentration of 20 cfu/ml of carbapenemase gene containing *P. aeruginosa* and *E. cloacae* bacteria as targets (VIM and KPC respectfully) was used. As seen in the results, 4 out of 4 or 3 out of 4 of the replicates provided positive detection with KPC and VIM targets (respectively). The cPCR protocol was performed with 6 preamplification steps each having 11 cycles. Pm_VIM_01/02/5 are probes immobilized to biochip, complementary to amplified VIM variant used as target in 20 cfu/ml concentration. Pm_kpc_01/02/03 are probes immobilized to biochip, complementary to amplified KPC target in 20 cfu/ml concentration.

DETAILED DESCRIPTION OF EMBODIMENTS

Figure 1:
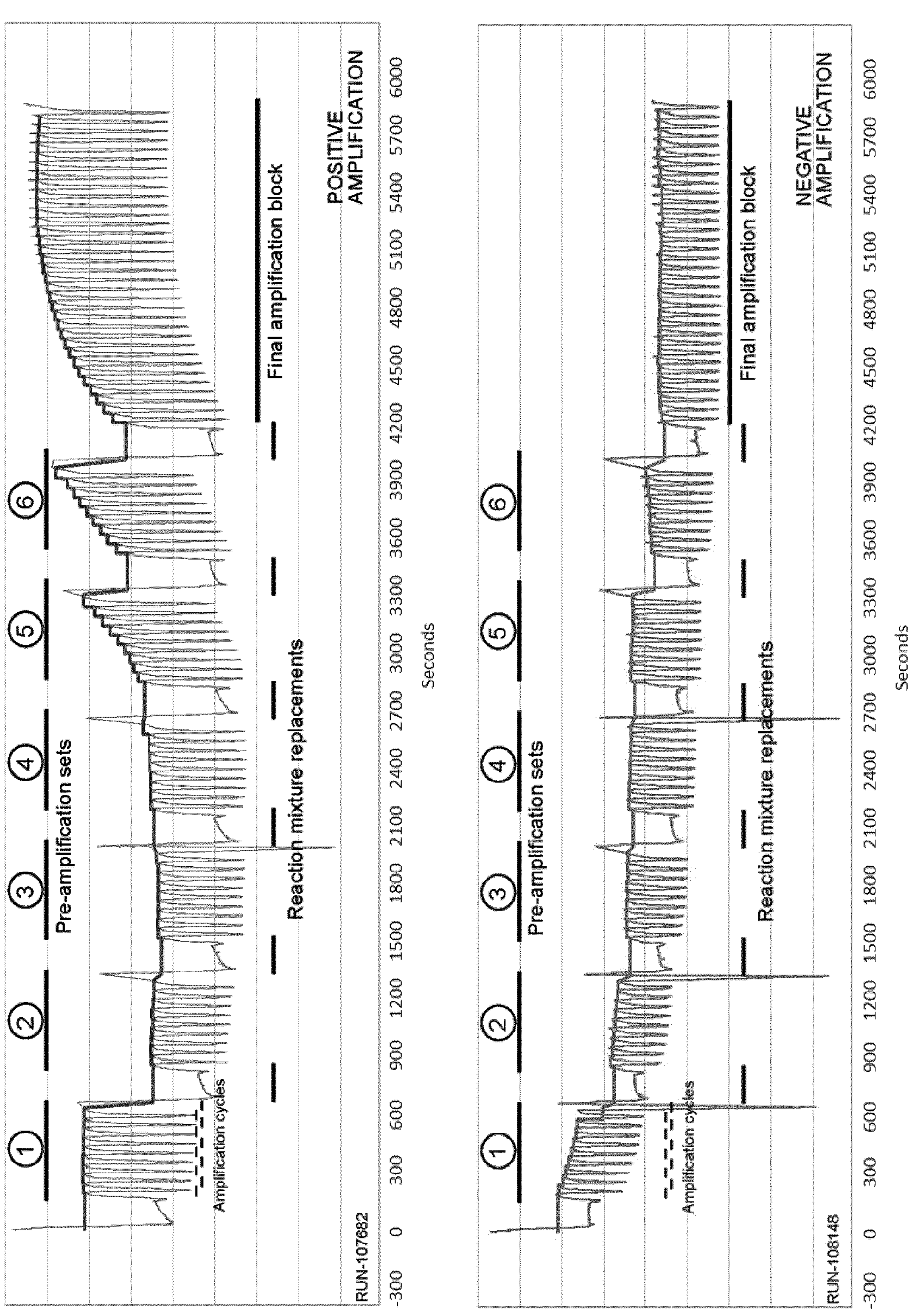
FIG. 1. Results of a cumulative PCR (cPCR) assay. Examples of qPCR detection from positive and negative sample when using cPCR protocol with 1 initial filling+5 refills of a chamber with 10 pre-amplification cycles in a system containing two reaction chambers having a volume of 20 μL. A dilute, ~10 cfu/mL bacterial sample solution is introduced into a cumulative PCR assay. In the cPCR process, 6 pre-amplification steps, each with 5 PCR cycles were performed. In the refill steps, 50% reaction mixture exchange of a total PCR reaction volume of 20 μL was used, thus altogether 70 μL of the input sample was pre-amplified per chamber. A clear detection with apparent quantification cycle (Cq~cycle) 15 is observed in the amplification curves shown, illustrating the increased sensitivity achieved with cPCR.

In the present description, the term "system" or "fluidic system" means an integrated system one or more chambers, ports, and channels that are interconnected and in fluid communication and designed for carrying out an analytical reaction or process, either alone or in cooperation with an appliance or instrument, i.e. a receiving station or device, that provides support functions, such as sample introduction, fluid and/or reagent driving means, temperature 10 control, and a detection system. Said fluidic system may further include valves, pumps, and specialized functional coatings on their interior walls, e.g. to prevent adsorption of sample components or reactants. Such devices are usually fabricated in or as a solid substrate, which may be glass, plastic, or other solid polymeric materials, and typically have a planar format or part for ease of detecting and monitoring sample and reagent movement, especially via optical or electrochemical methods. Examples of fluidic systems are disclosed in WO2012066239 and WO2015078998. It is also to be noted that the liquid sample and reagents suitable for amplification reactions can be transferred and mixed in the present system by natural diffusion.

In the context of the present description, the term "amplicon" means the product of a nucleic acid amplification reaction. Amplicons may be produced by a variety of amplification reactions whose products are multiple replicates of the sequence of one or more target nucleic acids, i.e. template(s). A target nucleic acid sequence or polynucleotide may be either single-stranded or in a duplex with its complementary sequence. Generally, amplification reactions producing amplicons are template-driven in that hybridization of oligonucleotides, i.e. primers, to a target sequence or its complement is required for the creation of amplicons. Said template-driven reactions are usually primer extension reactions mediated by a nucleic acid polymerase. Such reactions include polymerase chain reactions (PCRs). The PCR having been mentioned by way of example, other techniques of amplification may also be used, including the Reverse Transcriptase PCR (RT-PCR), the Rapid Amplification of cDNA Ends (RACE), the Rolling Circle Amplification (RCA), the Nucleic Acid Sequence Based Amplification (NASBA), the Transcription Mediated Amplification (TMA), the Ligase Chain Reaction. The isothermal amplification techniques may be advantageous because they are based on various enzymes that make useless the step of denaturizing the nucleic acids at 95° C. An amplification reaction may be a "real-time" amplification if a detection chemistry is available that permits a reaction product to be measured as the amplification reaction progresses.

The term "fluidly closable" in reference to an amplification reaction means that the reaction takes place within one or more vessels, chambers, valves, and/or passages, preferably interconnected and in communication with one another, comprising openings or channels which can be controllably arranged to such positions that in one liquids may pass and in another liquids may not pass (i.e. "selectably in fluidic communication" or "selectably in a liquid connection).

A "reaction mixture" means herein a solution containing all the necessary reagents for performing an amplification reaction, which may include, but not be limited to, a DNA template, an enzyme with DNA polymerase activity, target-specific oligonucleotides, dNTPs, NTPs, buffering agents to maintain pH at a selected level during a reaction, salts, co-factors, scavengers, and the like.

A "master mix" is a premixed concentrated liquid solution or a dried composition that preferably has all of the components of the reaction mixture that are not target-specific such as an enzyme with DNA polymerase activity, dNTPs, NTPs, buffering agents to maintain pH at a selected level during a reaction, salts, co-factors, scavengers, and the like (e.g. oligonucleotide primers and probes can be considered as target-specific components). However, in the present embodiments master mix may also comprise target-specific oligonucleotides. In a dried form, the master mix can be in a form of a coating on the inner wall of a chamber, such as a sample reservoir or a reagent reservoir, channel, or tube, or on a filter, and dissolves to a liquid when the liquid, such as a sample, is directed into said chamber, channel, filter or tube and the coating comes into contact with the liquid.

As used herein, the term "oligonucleotide" refers to any polymer of two or more of nucleotides, nucleosides, nucleobases or related compounds used as a reagent in the DNA amplification methods of the present disclosure. The oligonucleotide may be DNA and/or RNA and/or analogs thereof. The term oligonucleotide does not denote any particular function to the reagent; rather, it is used generically to cover all such reagents described herein. As used herein, an oligonucleotide can be virtually any length, limited only by its specific function in the nucleic acid amplification reaction. Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. Oligonucleotides may be modified in any way, as long as a given modification is compatible with the desired function of a given oligonucleotide. One of ordinary skill in the art can easily determine whether a given modification is suitable or desired for any given oligonucleotide of the present disclosure. Modifications include, but are not limited to base modifications, sugar modifications and backbone modifications. In the present disclosure, target-specific oligonucleotide primers and/or probes can be stored in a dried form in the cartridge/system such as in the form of dried coating on the inner wall of a chamber, such as a sample reservoir or a reagent reservoir, channel, or tube, or on a filter, and dissolve to a liquid when the liquid, such as a sample, is directed into said chamber, filter, channel or tube and the coating comes into contact with the liquid. In another preferred embodiment, the oligonucleotides are provided in the form of a liquid solution, which is, e.g., present in the sample reservoir or a reagent reservoir.

As used herein, the term "reaction", "amplifying" or "amplification" refers generally to cycling polymerase-mediated exponential amplification of nucleic acids employing primers that hybridize to complementary strands, as described for example in Innis et al, PCR Protocols: A Guide to Methods and Applications, Academic Press (1990). Devices have been developed that can perform thermal cycling reactions with compositions containing fluorescent indicators which are able to emit a light beam of a specified wavelength, read the intensity of the fluorescent dye, and display the intensity of fluorescence after each cycle. The amplification product contains a sequence having sequence identity with a target nucleic acid sequence or its complement and can be detected with, for example, an intercalating dye or a detection probe having specificity for a region of the target nucleic acid sequence or its complement. Amplification reagents can be detected also based on the length of the products, e.g. by gel electrophoresis. In one preferred embodiment of the present disclosure, the amplification products are detected by nucleic acid hybridization methods. In another preferred embodiment of the present disclosure, the nucleic acid amplification reaction of the present disclosure is preferably performed as a real-time PCR assay using a detector probe. The term "real-time PCR" is used in the current description for fluorescence-based PCR methods on photometric thermocyclers with the option for quantification of original template amounts. The method can include additional preamplification steps on a traditional thermocycler for a defined number of PCR-cycles. As used herein, the term "probe" refers to any of a variety of signaling molecules indicative of amplification.

The term "sample" means a quantity of material from a biological, environmental, forensic or medical source in which detection or measurement of target nucleic acids is sought. A sample may be processed into a liquid form, e.g., by extracting, precipitating or diluting, and may be further enriched or concentrated. A preferred sample is a DNA sample isolated or purified from a biological sample. Another preferred sample is a sample containing microbial cells such as bacterial cells isolated from a complex biological sample. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a human or animal patient including, but not limited to cultures, blood, saliva, cerebrospinal fluid, pleural fluid, milk, lymph, sputum, semen, needle aspirates, and broncho-alveolar lavage. Environmental samples include environmental material such as surface matter, soil, water and industrial samples, as well as samples obtained from food and dairy processing instruments, apparatus, equipment, utensils, disposable and non-disposable items. In this description, the term "sample" can also refer to a mixture of any of the above-mentioned samples with reagents suitable for nucleic acid amplification reaction, preferably "a master mix" as defined above. In the present disclosure, this mixture preferably has a volume too large, such as 100-500 μL, for one regular size PCR reaction usually having a volume of 20-50 μL.

Cumulative Amplification

All DNA amplification technologies are typically of exponential in nature towards the amplification, where the amplified content of a previous cycle, e.g., in PCR or continuous reaction step in isothermal applications, serve as template for the succeeding amplification step, therefore yielding exponentially growing amount of amplicons/amplification product(s). The reaction sensitivity, as defined herein, is a consequence of the assay sensitivity and the number of initial template molecules present in the reaction. Therefore, the capability of applying larger volumes of the input sample to the reaction, being it 1) a diluted sample due to overcome inhibition; 2) a dilute sample by its nature; 3) an elution fraction from nucleic acids extraction/purification reaction; or 4) any sample with volume exceeding the volume that can be introduced to the amplification reaction, is of uttermost significance.

The present disclosure combines the exponential nature of nucleic acid amplification technologies with a controllable, preferably closed circuit fluidics, where a subset of the amplification reaction volume can be replaced between the amplification steps. In this way, a large volume of input sample can be processed, and theoretically a single target molecule present in the processed larger volume input sample, being beyond the volume capable to be introduced to the amplification reaction at once, is enough to be exponentially amplified in the reaction. The change ratio of the amplified reaction mixture present in a reaction chamber to the sample volume used for refilling is preferably at most 1:2-1:50, i.e. at most 50 vol %, 55 vol %, 60 vol %, 65 vol %, 70 vol %, 75 vol %, 80 vol %, 85 vol %, 90 vol %, 95 vol %, or 98 vol % of the amplified reaction mixture is replaced with an unamplified sample, wherein said unamplified sample preferably comprises reagents necessary for the amplification reaction.

In this method, the input sample is preferably mixed with the other constituents of the amplification reaction, either before loading to the closed circuit system or during the fluidics operation before the amplification reaction. This is then followed by a set of pre-amplification reactions, typically few cycles with PCR or a short time with isothermal amplification reactions, after which a certain fraction, but not all, of the amplification reaction is replaced with unprocessed/un-amplified reaction mixture of the input sample and other amplification reaction constituents.

Accordingly, in one aspect the present disclosure is directed to a method of determining the presence or absence of a target polynucleotide in a sample, the method comprising the steps of:

- i) subjecting an amplification reaction mixture in a reaction chamber to conditions amplifying a target polynucleotide, wherein said reaction mixture comprises reagents necessary for nucleic acid amplification and an aliquot of the sample;
- ii) replacing a portion of an amplified reaction mixture in said reaction chamber obtained from the amplification reaction of the previous step with a further unamplified aliquot of said sample and with further reagents necessary for nucleic acid amplification to obtain a mix of amplified reaction mixture and the unamplified sample;
- iii) subjecting the reaction mixture in said reaction chamber obtained from step ii) to conditions amplifying a target polynucleotide; and
- iv) optionally repeating a cycle of steps ii) and iii) a number of times required for subjecting a desired amount of the sample to the amplification reaction;
- v) optionally detecting the presence or absence of an amplicon formed in the preceding amplification steps to determine the presence or absence of the target polynucleotide in the sample.

In a preferred embodiment, the above method comprises initial steps of:

- mixing a sample with a master mix comprising reagents necessary for nucleic acid amplification;
- transferring a portion of the mix to a space, such as a chamber, preferably to said reaction chamber so that said portion forms an initial reaction mixture for a cumulative nucleic acid amplification reaction.

In a preferred embodiment, the above method comprises the steps of: (a) providing a nucleic acid amplification reaction system, said system being preferably at least partly fluidly closable, comprising a sample reservoir, a reaction chamber and a waste reservoir, wherein said sample reservoir is arranged to receive a sample and is in fluidic communication, preferably selectably, with the reaction chamber;

- (b) inserting a sample into said sample reservoir and contacting the inserted sample with a master mix to form a reaction mixture, wherein said master mix comprises reagents for performing a nucleic acid amplification reaction and wherein said master mix is present in said sample reservoir or said master mix is in a position which is in fluidic communication with said sample reservoir, or alternatively inserting a premixed sample into said sample reservoir, wherein said premixed sample comprises a mix of the sample and a mastermix comprising reagents for performing a nucleic acid amplification reaction, said premixed sample forming the reaction mixture;
- (c) transferring a portion of the reaction mixture obtained in step (b) to said reaction chamber;
- (d) subjecting the reaction mixture in said reaction chamber to conditions amplifying a target polynucleotide to form an amplicon, whenever such target polynucleotide is present in the reaction mixture;
- (e) replacing part of the amplified reaction mixture in said reaction chamber with a further portion of the reaction mixture obtained in step (b) by transferring said further portion of the reaction mixture obtained in step (b) to the reaction chamber, wherein a part of the liquid present in said reaction chamber is moved from the reaction chamber to the waste reservoir, the volume of said part of liquid preferably corresponding to the volume of said further portion;
- (f) repeating a cycle of steps (d) and (e) a number of times required for subjecting a desired amount of the reaction mixture obtained in step b) to the amplification reaction, preferably the cycle of steps (d) and (e) is repeated in step (f) so that the subsequent step (g) follows after step (d); and
- (g) optionally detecting the presence or absence of the amplicon formed in the preceding amplification steps (d) to determine the presence or absence of the target polynucleotide in the sample.

In another preferred aspect, the present disclosure provides a method of determining the presence or absence of a target polynucleotide in a sample, the method comprising the steps of:

- (a) providing a nucleic acid amplification reaction system, said system being preferably at least partly fluidly closable, comprising a sample reservoir, a reagent reservoir, a reaction chamber and a waste reservoir, wherein said sample reservoir is arranged to receive a sample and said sample reservoir is in fluidic communication, preferably selectably, with the reaction chamber and wherein said reagent reservoir comprises a master mix comprising reagents for performing a nucleic acid amplification reaction and said reagent reservoir is in fluidic communication, preferably selectably, with the reaction chamber;

(b) inserting a sample into said sample reservoir;

(c) transferring at least a portion of the sample from the sample reservoir to said reaction chamber and at least a portion of the master mix from the reagent reservoir to said reaction chamber to form a reaction mixture in said reaction chamber;

(d) subjecting the reaction mixture in said reaction chamber to conditions amplifying the target polynucleotide to form an amplicon, whenever such target polynucleotide is present in the reaction mixture;

(e) replacing part of the amplified reaction mixture subjected to said conditions with a further portion of the sample and with a further portion of the master mix by transferring said further portions of the sample and the master mix to the reaction chamber, wherein part of the liquid present in said reaction chamber is moved from the reaction chamber to the waste reservoir, the volume of said part of liquid preferably corresponding to the volume of said further portions;

(f) repeating a cycle of steps (d) and (e) a number of times required for subjecting a desired amount of the sample to the amplification reaction, preferably the cycle of steps (d) and (e) is repeated in step (f) so that the subsequent step (g) follows after step (d);

(g) optionally detecting the presence or absence of an amplicon formed in the preceding amplification steps to determine the presence or absence of the target polynucleotide in the sample.

In a preferred embodiment, said detecting in step (g) comprises further amplification steps in order to exponentially amplify the amplicon formed in the cycle of preamplification steps (d).

The detection of the amplicon in step (g), whenever present, may be performed by means of various techniques. Generally, the detection of target molecules is performed by implementing molecular recognition mechanisms, which indicates the presence of a searched substance by means of a detectable optical signal. For instance, the amplification step may allow marking the amplicons, for example by incorporating tagged nucleotides (i.e. carrying a detectable element). The choice of the tag (detectable element) depends on the strategy of detection used. Within the framework of optical reading in light-detection molecular recognition (optical transduction), the tag may be an organic fluorophore or inorganic nanoparticles.

In step (g), the detection may be conducted in a separate detection chamber. Preferably, the detection chamber comprises an affinity biosensor for detecting the presence of specific target molecules in the sample. The affinity biosensors preferably interact with the target molecule by hybridization or e.g. by ligation. The capture of the amplification products, or amplicons, on a surface is a technique that is well-known to the one skilled in the art.

In preferred embodiments, the detection chamber comprises a biochip. The biochip systems are presently widely used for the detection and the measurement of specific substances in complex samples. With such a biochip, the identity and quantity of a target molecule in a sample are measured by measuring the level of association of the target sequence with probes specifically provided for said sequence. In the DNA biochip technologies, a set of probe nucleic acids, each having a defined sequence, is immobilized on a solid support or substrate in such a way that each probe occupies a predetermined position. Once the set of probes immobilized, the biochip is placed into contact with a sample in such a way that the complementary sequences can be combined with an immobilized probe, for example by hybridization, association or linking to the probe. After the elimination of the non-associated material, the associated sequences are detected and measured.

According to this embodiment in which the biochip detection is used, the detection and quantification of the interaction between the target molecules and the probes are performed by an optical detection device: a light radiation of a first given wavelength excites chromophores linked to the target molecules. The light emitted by the chromophores at a second wavelength, in response to their luminous excitation is then collected by a collecting device.

In preferred embodiments, steps (d) and (e) are combined so that part (i.e. a subset) of the amplified reaction mixture is replaced with a further portion of the premixed sample and the master mix (or separate inputs thereof) by continuously transferring said further portion of the premixed sample and the master mix to the reaction chamber, wherein a volume of liquid, preferably corresponding to the volume of said further portion entering the reaction chamber, is moved from the reaction chamber to the waste reservoir. This embodiment thus provides a cumulative amplification reaction with a continuous sample input.

In preferred embodiments, in step (e), part of the amplified reaction mix can also be replaced with further sample and nucleic acid amplification reagents by transferring said part of the amplified reaction mixture from the reaction chamber to the waste reservoir and adding further sample and nucleic acid amplification reagents with the remaining reaction mix in the reaction chamber.

In other preferred embodiments, the mixing steps of the present methods comprises forming the reaction mixture in the sample reservoir, in a separate mixing reservoir in connection with the reaction chamber or before the insertion step.

In other preferred embodiments, said nucleic acid amplification reaction system comprises a reaction chamber selectably in fluid communication with at least one of the following: a waste reservoir, a sample reservoir, and optionally a reagent reservoir containing amplification reagents, wherein at least one of the reservoirs is fluidly closable, more preferably each of the reservoirs and the reaction chamber are fluidly closable. Preferably, the mixing step of the present methods comprises forming the reaction mixture in the reagent reservoir and transferring the reaction mixture to the reaction chamber.

In other preferred embodiments, the amplification reaction is a polymerase chain reaction (i.e. a PCR reaction) or an isothermal amplification reaction.

In other preferred embodiments, said sample is a biological, environmental, forensic, food or medical sample or a DNA sample isolated or purified therefrom.

In another aspect, the present disclosure is directed to a nucleic acid amplification reaction system, preferably a fluidly closable system, for performing a cumulative amplification reaction, the system comprising:

a reaction chamber in fluidic communication, preferably selectably, with a sample reservoir and a waste reservoir, wherein said sample reservoir is arranged to receive a sample, and preferably at least one of the reservoirs is fluidly closable; and means for performing the steps of: (a) transferring a portion of the contents of the sample reservoir to the reaction chamber; (b) subjecting the contents of the reaction chamber to conditions supporting nucleic acid amplification reactions;

(c) replacing part of the contents present in the reaction chamber with a further portion of the contents of said sample reservoir to obtain a mix of amplified reaction and the unamplified sample, wherein a volume of liquid, preferably corresponding to the volume of said further portion entering the reaction chamber, is moved from the reaction chamber to the waste reservoir, and (d) repeating a cycle of steps (b) and (c) a number of times required for subjecting a desired amount of the sample to the amplification reaction, wherein step (c) is performed at controlled intervals or continuously. Preferably, said means comprise a pump, preferably operationally associated with a valve, such as a rotary valve.

In another aspect, the present disclosure is directed to a nucleic acid amplification reaction system, preferably a fluidly closable system, for performing a cumulative amplification reaction, the system comprising:

a reaction chamber in fluid communication, preferably selectably, with a sample reservoir, a waste reservoir, and a reagent reservoir containing a master mix comprising nucleic acid amplification reagents, and preferably at least one of the reservoirs is fluidly closable, wherein said sample reservoir is arranged to receive a sample and is in fluidic communication, preferably selectably, with the reaction chamber; and means for performing repeated cycles of steps: (a) transferring a portion of the sample from the sample reservoir and a portion of the master mix from the reactant reservoir to the reaction chamber; (b) subjecting the contents in the reaction chamber to conditions supporting nucleic acid amplification reactions; (c) replacing part of the contents of the reaction chamber with further portions of the sample and master mix to obtain a mix of amplified reaction and the unamplified sample, wherein a volume of liquid, preferably corresponding to the volumes of said further portions entering the reaction chamber, is moved from the reaction chamber to the waste reservoir, and (d) repeating a cycle of steps (b) and (c) a number of times required for subjecting a desired amount of the sample to the amplification reaction, wherein step (c) is performed at desired intervals or continuously. Preferably, said means comprise a pump, preferably operationally associated with a valve, such as a rotary valve.

In a preferred embodiment, said systems comprise a computer executable program to control the performance of the cumulative amplification reaction. The program preferably comprising instructions for: (a) metering of a portion of a sample or a sample premixed with a master mix, and optionally a separate portion of amplification reagents, i.e. master mix, for transferring said portion(s) into a reaction chamber, preferably by controlling opening and closing of channel valves interconnecting a sample reservoir and the reaction chamber and optionally a reagent reservoir; (b) optionally thermally controlling the amplification cycle in the reaction chamber (in case of isothermal amplification, thermal control is not required); and (c) optionally metering a portion of the reaction mix subjected to the amplification cycle moved into a waste reservoir; (d) repeating steps (a) to (c) until a predetermined or desired amount of the sample or the premixed sample is transferred to the reaction chamber; (e) initiating a subsequent amplification cycle in the reaction chamber for the detection of an amplified target sequence; (f) detecting the presence or absence of the target sequence in the sample. The present disclosure may thus also be directed to a computer program comprising instructions which, when the program is executed by a computer, cause the computer to control the performance of the steps of the methods of the present disclosure or a computer program comprising instructions or software code adapted to perform or control the performance of said methods or systems.

In preferred embodiments, said system comprises a cartridge comprising said sample reservoir, reaction chamber and waste reservoir and optionally a reagent reservoir. In a more preferred embodiment, said system further comprises a detection chamber for performing the detection step (f).

In further preferred embodiments, said system comprises a device for receiving the cartridge, said device being for controlling the functions of the cartridge. These functions include in particular the control of the fluidic flowing (such as control of the actuation of the integrated valves of the cartridge) and the control of the temperature of the reaction chambers or areas.

In an alternative embodiment, the method of the present disclosure comprises the steps of:

i) subjecting an amplification reaction mixture in a reaction chamber to conditions amplifying a target polynucleotide, wherein said reaction mixture comprises reagents necessary for nucleic acid amplification and an aliquot of the sample;

ii) replacing the amplified reaction mixture in said reaction chamber obtained from the amplification reaction of the previous step with a further unamplified aliquot of said sample and with further reagents necessary for nucleic acid amplification, wherein said amplified reaction mixture is moved to a store reservoir;

iii) subjecting the reaction mixture comprising said unamplified aliquot in said reaction chamber to conditions amplifying a target polynucleotide;

iv) repeating a cycle of steps ii) and iii) a number of times required for subjecting a desired amount of the sample to the amplification reaction;

v) subjecting an aliquot of the amplified reaction mixture present in said store reservoir to a further amplification reaction in order to detect a product pre-amplified in steps ii) and iii).

The present disclosure is also directed to an alternative system for performing a cumulative amplification reaction, the system comprising:

a reaction chamber in fluidic communication with a sample reservoir and a store reservoir, wherein said sample reservoir is arranged to receive a sample; and means for performing the steps of: (a) transferring a portion of the contents of the sample reservoir to the reaction chamber; (b) subjecting the contents of the reaction chamber to conditions supporting nucleic acid amplification reactions; (c) replacing the contents present in the reaction chamber with a further portion of the contents of said sample reservoir transferred to the reaction chamber, wherein a volume of liquid present in the reaction chamber is moved from the reaction chamber to the store reservoir, (d) repeating a cycle of steps (b) and (c) a number of times required for subjecting a desired amount of the sample to the amplification reaction, wherein step c) is performed at desired intervals or continuously, and (e) subjecting an aliquot of the amplified reaction mixture present in said store reservoir to a further amplification reaction.

Reference throughout this specification to one embodiment or an embodiment means that a particular feature, structure, or characteristic described in connection with the embodiment is included in at least one embodiment of the present disclosure. Thus, appearances of the phrases “in one embodiment” or “in an embodiment” in various places throughout this specification are not necessarily all referring to the same embodiment. Where reference is made to a numerical value using a term such as, for example, about or substantially, the exact numerical value is also disclosed.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

It will be obvious to a person skilled in the art that, as the technology advances, the inventive concept can be implemented in various ways. The present disclosure and its embodiments are not limited to the examples described above but may vary within the scope of the claims.

EXPERIMENTAL SECTION

Example 1. Calculations of Potential Template Amplification in Cumulative Amplification Reactions In the present calculations, a reaction mixture volume (110 μL) exceeding the capabilities of a single amplification reaction is subjected as aliquots to 10 pre-amplification steps. Each pre-amplification step contains 5 PCR cycles with reaction volume of 20 μL, followed by 45 main amplification cycles. Perfect exponential ($2^n$) amplification efficiency for the pre-amplification steps is assumed in the calculations. It is also assumed that there is only one amplifiable molecule (i.e. a template) in the processed reaction mixture volume comprising a mix of necessary reagents for the PCR reaction and a sample.

The calculation was performed using 5 PCR cycles in each pre-amplification step and having 50% of the reaction volume of 20 μL (i.e. 10 μL) replaced with the remaining reaction mixture between pre-amplification steps. The calculated amounts of amplicons (i.e. template molecules) are listed in Table 1.

From Table 1, it can be seen that no matter in which of the 10 fractions of the 110 μL of reaction mixture volume the single template molecule is introduced to the pre-amplification process, cumulative amplification can provide enough material for the final PCR amplification for true positive detection.

Comparison of theoretical single molecule sensitivity in cumulative amplification and regular PCR (with reaction volume of 20 μL): in the present case, there would be only 20/110=18% chance of getting true positive result. In other words, in most cases, the regular PCR would have given a false negative result due to lack of sufficient amount of template molecules to be introduced to the PCR reaction.

Example 2. A Cumulative PCR (cPCR) Assay with a Blood Sample Derived Eluate Potentially Comprising Sepsis Bacteria Volume of 310 μL of an eluate derived from a blood sample is mixed with master mix (primers, polymerase enzyme, nucleotides and buffer components) for a cumulative PCR reaction so that the eluate content in total reaction mixture is 40%. This premixed reaction solution of 750 ul is subjected to 6 pre-amplification cycles as 22 aliquots in two PCR chambers (11/chamber). After the 6 cycles of amplification for the initial 20 μL aliquot, the PCR chamber is further filled with 20 μL aliquot of the premixed reaction solution. The fraction of the first aliquot moves forward from the PCR chamber to the waste reservoir while filling the reaction chamber with new aliquot. The 10 refills have a volume of 20 μL each. During the process of inserting a filling aliquot to the reaction chamber, a corresponding volume of liquid is moved from the reaction chamber to the waste reservoir. The refill of 20 μL to 20 μL PCR chamber does not completely remove previous volume in the chamber but instead part of the volume with possible preamplified amplicons will stay and be subjected to next preamplification cycles.

The change ratio of the amplified reaction mixture present in the reaction chamber to the aliquot volume used for refilling have been determined using Comsol simulation. With 7 μL filling, no loss of refill volume occurs by liquid going through the PCR chamber. With 20 μL refill, part of added refill goes through the chamber already during the filling step. However, our results confirmed that the described filling procedure ensures that a maximum amount of reaction solution is processed in PCR and sufficient amount of amplification products produced in any stage of the preamplifications steps are carried to the next pre-amplification step and to the final amplification required for a subsequent detection step.

The whole cPCR process is run on a Novodiag cartridge (Mobidiag, Espoo, Finland) and detected by hybridization in Novodiag instrument (Mobidiag, Espoo, Finland) (see FIG. 2). The detection can also be done in qPCR in the Novodiag instrument (see FIG. 1 as an example).

TABLE 1

Calculated amounts of amplicons (i.e. template molecules) in cumulative preamplification steps using 5 PCR cycles in each pre-amplification step and having 50% of the amplification mixture replaced between pre-amplification steps (amplification efficacy of 100% is assumed).

| | Replacement volume (%) | | | | | | | | | |
|---|---|---|---|---|---|---|---|---|---|---|
| | 50% | | Pre-amplification cycles | | 5 | | | | | |
| | Pre-amplification set | | | | | | | | | |
| | 1 | 2 | 3 | 4 | 5 | 6 | 7 | 8 | 9 | 10 |
| | Processed reaction/sample volume (μL) | | | | | | | | | |
| | 20 | 30 | 40 | 50 | 60 | 70 | 80 | 90 | 100 | 110 |
| Input target molecules | 0 | 0 | 0 | 0 | 0 | 0 | 0 | 0 | 0 | 1 |
| Template molecules after pre-amplification set | 0 | 0 | 0 | 0 | 0 | 0 | 0 | 0 | 0 | 32 |
| Input target molecules | 0 | 0 | 0 | 0 | 0 | 0 | 0 | 0 | 1 | 0 |
| Template molecules after pre-amplification set | 0 | 0 | 0 | 0 | 0 | 0 | 0 | 0 | 32 | 512 |

TABLE 1-continued

Calculated amounts of amplicons (i.e. template molecules) in cumulative preamplification steps using 5 PCR cycles in each pre-amplification step and having 50% of the amplification mixture replaced between pre-amplification steps (amplification efficacy of 100% is assumed).

| | Replacement volume (%) | | | | | | | | | |
|---|---|---|---|---|---|---|---|---|---|---|
| | 50% | Pre-amplification cycles | | | 5 | | | | | |
| | Pre-amplification set | | | | | | | | | |
| | 1 | 2 | 3 | 4 | 5 | 6 | 7 | 8 | 9 | 10 |
| | Processed reaction/sample volume (µL) | | | | | | | | | |
| | 20 | 30 | 40 | 50 | 60 | 70 | 80 | 90 | 100 | 110 |
| Input target molecules | 0 | 0 | 0 | 0 | 0 | 0 | 0 | 1 | 0 | 0 |
| Template molecules after pre-amplification set | 0 | 0 | 0 | 0 | 0 | 0 | 0 | 32 | 512 | 8192 |
| Input target molecules | 0 | 0 | 0 | 0 | 0 | 0 | 1 | 0 | 0 | 0 |
| Template molecules after pre-amplification set | 0 | 0 | 0 | 0 | 0 | 0 | 32 | 512 | 8192 | 131072 |
| Input target molecules | 0 | 0 | 0 | 0 | 0 | 1 | 0 | 0 | 0 | 0 |
| Template molecules after pre-amplification set | 0 | 0 | 0 | 0 | 0 | 32 | 512 | 8192 | 131072 | 2097152 |
| Input target molecules | 0 | 0 | 0 | 0 | 1 | 0 | 0 | 0 | 0 | 0 |
| Template molecules after pre-amplification set | 0 | 0 | 0 | 0 | 32 | 512 | 8192 | 131072 | 2097152 | 33554432 |
| Input target molecules | 0 | 0 | 0 | 1 | 0 | 0 | 0 | 0 | 0 | 0 |
| Template molecules after pre-amplification set | 0 | 0 | 0 | 32 | 512 | 8192 | 131072 | 2097152 | 33554432 | 536870912 |
| Input target molecules | 0 | 0 | 1 | 0 | 0 | 0 | 0 | 0 | 0 | 0 |
| Template molecules after pre-amplification set | 0 | 0 | 32 | 512 | 8192 | 131072 | 2097152 | 33554432 | 536870912 | 8589934592 |
| Input target molecules | 0 | 1 | 0 | 0 | 0 | 0 | 0 | 0 | 0 | 0 |
| Template molecules after pre-amplification set | 0 | 32 | 512 | 8192 | 131072 | 2097152 | 33554432 | 536870912 | 8589934592 | 1.3744E+11 |
| Input target molecules | 1 | 0 | 0 | 0 | 0 | 0 | 0 | 0 | 0 | 0 |
| Template molecules after pre-amplification set | 32 | 512 | 8192 | 131072 | 2097152 | 33554432 | 536870912 | 8589934592 | 1.3744E+11 | 2.199E+12 |

TABLE 2

Example of reaction conditions for a cumulative PCR assay: Cumulative PCR protocol

| | | |
|---|---|---|
| 95° C., 120 s | Initial denaturation | 11 × Pre-amplification |
| 95° C., 10 s | ×6 preamplification cycles | (11 × 20 ul = 220 ul/ PCR chamber) |
| 60° C., 25 s | | |
| 95° C., 120 s | Initial denaturation | Final amplification |
| 95° C., 10 s | ×35 amplification cycles | (20 ul/PCR chamber) |
| 60° C., 25 s | | |
| | Processed reaction mixture volume: | 480 ul/750 ul |
| | Processed eluate volume: | 192 ul/310 ul (62%) |

The invention claimed is:

1. A nucleic acid amplification method for determining the presence or absence of a target polynucleotide in a sample, the method comprising the steps of:

i) subjecting a first reaction mixture in a reaction chamber to conditions for amplifying a target polynucleotide, wherein said first reaction mixture comprises reagents necessary for performing a nucleic acid amplification and an aliquot of the sample, thereby performing an amplification reaction and providing an amplified reaction mixture;

ii) replacing a portion of the amplified reaction mixture in said reaction chamber obtained from the amplification reaction of the previous step with a further unamplified aliquot of said sample and with further reagents necessary for nucleic acid amplification to obtain a mix of amplified reaction mixture and the unamplified sample, thereby providing a subsequent reaction mixture;

iii) subjecting the subsequent reaction mixture in said reaction chamber obtained from step ii) to conditions for amplifying a target polynucleotide;

iv) optionally repeating a cycle of steps ii) and iii) a number of times required for subjecting a desired amount of the sample to the amplification reaction; and v) detecting the presence or absence of an amplicon formed in the preceding amplification steps to determine the presence or absence of the target polynucleotide in the sample.

2. The method according to claim 1, wherein the reaction chamber is in fluidic communication with a sample reservoir, and wherein (a) the method further comprises the step of inserting a sample into said sample reservoir and contacting the inserted sample with a master mix to form the first reaction mixture, wherein said master mix comprises reagents for performing a nucleic acid amplification reaction and wherein said master mix is present in said sample reservoir or said master mix is in a position which is in fluidic communication with said sample reservoir, or alternatively inserting a premixed sample into said sample reservoir, wherein said premixed sample comprises a mix of the sample and a master mix comprising reagents for performing a nucleic acid amplification reaction, said premixed sample forming the first reaction mixture;

(b) the method further comprises the step of transferring a portion of the first reaction mixture obtained in step (a) from the sample reservoir to said reaction chamber;

(c) step i) is performed following step (b);

(d) step ii) comprises replacing part of the amplified reaction mixture in said reaction chamber with a further portion of the first reaction mixture obtained in step (a) by transferring said further portion of the first reaction mixture obtained in step (a) to the reaction chamber, wherein a part of the liquid present in said reaction chamber is moved from the reaction chamber to a waste reservoir, wherein the mixture remaining in the reaction chamber is the subsequent reaction mixture provided by step ii); and (e) the method comprises step iv), whereby a cycle of steps ii) and iii) is repeated a number of times required for subjecting a desired amount of the first reaction mixture obtained in step (a) to the amplification reaction, and whereby one or more additional subsequent reaction mixtures are provided.

3. The method according to claim 2, wherein in step (a) said master mix which is present in said sample reservoir or in a position which is in fluidic communication with said sample reservoir is contacted with said sample in a dried form.

4. The method according to claim 2, wherein steps i) and ii) are combined so that the first or subsequent reaction mixture present in the reaction chamber is continuously replaced with a further portion of the sample by continuously transferring said further portion of the first reaction mixture obtained in step (a) to the reaction chamber, wherein a volume of liquid corresponding to the volume of said further portion of said first reaction mixture is simultaneously moved from the reaction chamber to the waste reservoir.

5. The method according to claim 1, wherein the reaction chamber is selectably in fluid communication with at least one of the following: a sample reservoir and a waste reservoir, wherein at least one of the reservoirs or the reaction chamber is fluidly closable.

6. The method according to claim 1, wherein said sample and said reagents necessary for performing the nucleic acid amplification are premixed before step i) to obtain the first reaction mixture.

7. The method according to claim 1, wherein the reaction chamber is in fluidic communication with a sample reservoir and a reagent reservoir, wherein said sample reservoir is arranged to receive the sample, wherein said reagent reservoir comprises a master mix comprising the reagents necessary for performing the nucleic acid amplification reaction, and wherein (a) the method further comprises the step of inserting a sample into said sample reservoir;

(b) the method further comprises the step of transferring at least a portion of the sample from the sample reservoir to said reaction chamber and at least a portion of the master mix from the reagent reservoir to said reaction chamber to form the first reaction mixture in said reaction chamber;

(c) step i) is performed following step (b);

(d) step ii) comprises replacing part of the amplified reaction mixture subjected to said conditions with a further portion of the sample and with a further portion of the master mix by transferring further portions of the sample and the master mix to the reaction chamber, wherein a part of the liquid present in said reaction chamber is moved from the reaction chamber to a waste reservoir, wherein the mixture remaining in the reaction chamber is the subsequent reaction mixture provided by step ii); and (e) the method comprises step iv), whereby a cycle of steps ii) and iii) is repeated a number of times required for subjecting a desired amount of the sample to the amplification reaction, and whereby one or more additional subsequent reaction mixtures are provided;

wherein steps i) and ii) are optionally combined so that the first or subsequent reaction mixture present in the reaction chamber is continuously replaced with a further portion of the sample and a further portion of the master mix by continuously transferring said further portions of the sample and master mix to the reaction chamber, wherein a volume of liquid present in said reaction chamber is simultaneously moved from the reaction chamber to the waste reservoir; and wherein the reaction chamber is selectably in fluid communication with at least one of the following: the waste reservoir, the sample reservoir, and the reagent reservoir containing the master mix, wherein at least one of the reservoirs is fluidly closable.

8. The method according to claim 7, wherein the amplification reaction is a polymerase chain reaction or an isothermal amplification reaction.

9. The method according to claim 7, wherein said sample is a biological, environmental, forensic, food or medical sample.

10. A nucleic acid amplification method for determining the presence or absence of a target polynucleotide in a sample, the method comprising the steps of:

i) subjecting a first reaction mixture in a reaction chamber to conditions for amplifying a target polynucleotide, wherein said first reaction mixture comprises reagents necessary for nucleic acid amplification and an aliquot of the sample, thereby performing an amplification reaction and providing an amplified reaction mixture;

ii) replacing the amplified reaction mixture in said reaction chamber obtained from the amplification reaction of the previous step with a further unamplified aliquot of said sample and with further reagents necessary for nucleic acid amplification, wherein said amplified reaction mixture is moved to a store reservoir, thereby providing a subsequent reaction mixture;

iii) subjecting the subsequent reaction mixture comprising said unamplified aliquot in said reaction chamber to conditions amplifying a target polynucleotide;

iv) repeating a cycle of steps ii) and iii) a number of times required for subjecting a desired amount of the sample to the amplification reaction;

v) subjecting an aliquot of the amplified reaction mixture present in said store reservoir to a further amplification reaction in order to detect a product pre-amplified in steps ii) and iii).

* * * * *